(12) United States Patent
Kim (10) Patent No.: US 10,426,645 B2
(45) Date of Patent: *Oct. 1, 2019

(54) POLYMERIC STENT AND METHODS OF MANUFACTURING THE SAME

(71) Applicant: Suntech Co., Ltd., Seoul (KR)

(72) Inventor: Hyung-Il Kim, Seoul (KR)

(73) Assignee: DOTTER INTELLECTUAL PTE. LTD., Singapore (SG)

( * ) Notice: Subject to any disclaimer, the term of this patent is extended or adjusted under 35 U.S.C. 154(b) by 165 days.

This patent is subject to a terminal disclaimer.

(21) Appl. No.: 15/282,500

(22) Filed: Sep. 30, 2016

(65) Prior Publication Data

US 2017/0014251 A1    Jan. 19, 2017

Related U.S. Application Data

(62) Division of application No. 14/626,584, filed on Feb. 19, 2015, now Pat. No. 9,510,961.

(30) Foreign Application Priority Data

Feb. 26, 2014   (KR) .................. 10-2014-0022859

(51) Int. Cl.
*B29C 35/08* (2006.01)
*B23K 26/0622* (2014.01)
(Continued)

(52) U.S. Cl.
CPC .......... *A61F 2/915* (2013.01); *B23K 26/0624* (2015.10); *B23K 26/0676* (2013.01); *B23K 26/38* (2013.01); *B23K 26/402* (2013.01); *B29C 35/0805* (2013.01); *B29C 59/165* (2013.01); *A61F 2/82* (2013.01); *A61F 2002/91533* (2013.01); *A61F 2002/91541* (2013.01); *A61F 2002/91575* (2013.01); *A61F 2002/91583* (2013.01); *A61F 2210/0004* (2013.01); *A61F 2240/001* (2013.01); *B23K 2101/02* (2018.08); *B23K 2103/42* (2018.08); *B23K 2103/50* (2018.08); *B29C 35/08* (2013.01); *B29C 2035/0838* (2013.01);
(Continued)

(58) Field of Classification Search
CPC ........................................................ A61F 2/82
See application file for complete search history.

(56) References Cited

U.S. PATENT DOCUMENTS 5,508,378 A   4/1996   Ohara et al.
5,928,280 A   7/1999   Hansen et al.
(Continued)

FOREIGN PATENT DOCUMENTS

WO   2007/142736 A2   12/2007

OTHER PUBLICATIONS

European Office Action dated Aug. 28, 2017 for European Application No. 15156735.1, pp. 1-4.
(Continued)

*Primary Examiner* — Jacqueline Woznicki
(74) *Attorney, Agent, or Firm* — MH2 Technology Law Group, LLP (57) ABSTRACT

Methods of manufacturing polymeric stents by forming a pattern on a polylactic acid tube using a second harmonic generator laser and polylactic acid polymeric stents having a pattern formed using a second harmonic generator laser.

4 Claims, 5 Drawing Sheets

(51) Int. Cl.
  *B23K 26/067* (2006.01)
  *B23K 26/38* (2014.01)
  *B29C 59/16* (2006.01)
  *A61F 2/82* (2013.01)
  *B23K 101/02* (2006.01)
  *B29K 67/00* (2006.01)
  *A61F 2/915* (2013.01)
  *B23K 26/402* (2014.01)
  *B23K 103/00* (2006.01)
  *B29L 31/00* (2006.01)

(52) U.S. Cl.
  CPC .. *B29K 2067/046* (2013.01); *B29K 2995/006* (2013.01); *B29L 2031/7532* (2013.01)

(56) References Cited

U.S. PATENT DOCUMENTS

| | | | |
|---|---|---|---|
| 9,510,961 B2* | 12/2016 | Kim | B23K 26/402 |
| 2002/0065553 A1 | 5/2002 | Weber | |
| 2002/0108937 A1 | 8/2002 | Shapovalov et al. | |
| 2003/0151053 A1 | 8/2003 | Sun et al. | |
| 2004/0220660 A1 | 11/2004 | Shanley et al. | |
| 2007/0034615 A1 | 2/2007 | Kleine | |
| 2007/0156230 A1 | 7/2007 | Dugan et al. | |
| 2008/0275537 A1 | 11/2008 | Limon | |
| 2009/0319031 A1 | 12/2009 | Wang et al. | |
| 2010/0262223 A1 | 10/2010 | Kleiner | |
| 2011/0307050 A1 | 12/2011 | Harrington et al. | |
| 2015/0230946 A1 | 8/2015 | Al-Lamee et al. | |

OTHER PUBLICATIONS

Park, Seung-Bae, "Notice of Grounds of Rejection (Korean Office Action)," dated Jun. 27, 2014 for corresponding Korean Application No. 10-2014-0022859 filed Feb. 26, 2014, 14 pages (including translation).

Extended European Search Report dated Aug. 9, 2015 from European Patent Application No. 15156735.1, pp. 1-5.

Final Office Action dated May 19, 2016 for U.S. Appl. No. 14/626,584, pp. 1-26.

Non-Final Office Action dated Feb. 1, 2016 for U.S. Appl. No. 14/626,584, pp. 1-12.

Non-Final Office Action dated Sep. 8, 2017 for U.S. Appl. No. 15/338,890, pp. 1-10.

Final Office Action dated Oct. 5, 2017 for U.S. Appl. No. 14/626,481, pp. 1-9.

Non-Final Office Action dated May 19, 2017 for U.S. Appl. No. 14/626,481, pp. 1-7.

Non-Final Office Action dated Aug. 24, 2017 for U.S. Appl. No. 15/435,844, pp. 1-7.

* cited by examiner

POLYMERIC STENT AND METHODS OF MANUFACTURING THE SAME

CROSS REFERENCE TO RELATED APPLICATIONS

This application is a divisional of U.S. application Ser. No. 14/626,584 (Allowed), filed 19 Feb. 2015, which claims priority to and the benefit of Korean Patent Application No. 10-2014-0022859 filed in the Korean Intellectual Property Office on Feb. 26, 2014, the entire contents of which are incorporated herein by reference.

FIELD

The field of the invention relates to polymeric stents, and in particular methods of manufacturing such devices.

BACKGROUND

In general, stents are expandable medical prostheses, and are used within body vessels of humans for a variety of medical applications. Examples include intravascular stents for treating stenosis, and stents for maintaining openings in the urinary, biliary, tracheobronchial, esophageal, and renal tracts, and inferior vena cava.

Typically, prior to placement, a stent will be maintained in a compressed state and delivered by a device designed to position the compressed stent at a treatment site, and then allow the stent to expand once in position. Commonly, stents are delivered to the treatment site by passage through the lumen of body vessels.

For example, in percutaneous transluminal angioplasty, an implantable endoprosthesis, that is, a stent is introduced through a delivery device, and is passed through body vessel conduits to a treatment site. After the stent approaches the treatment site, the stent is typically mechanically expanded, usually with the aid of an inflatable balloon, thereby being expanded within the body vessel. The delivery device is then retreated and removed from the patient. The stent remains within the vessel at the treatment site as an implant.

SUMMARY

Various objects, features, aspects and advantages of the inventive subject matter will become more apparent from the following detailed description of preferred embodiments, along with the accompanying drawing figures in which like numerals represent like components.

The present disclosure provides polymeric stents and methods for their manufacture using a laser. Compared to prior art polymeric stents, the stents described herein have superior properties, for example, with respect to mechanical strength, thermal injury and/or low degradation, as compared to prior art designs.

In one aspect there is provided a method for manufacturing a polymeric stent, comprising: forming a pattern on a polylactic acid tube with a second harmonic generator laser in which a wavelength ranging from about 940 nm to 1552 nm or less is converted.

In another aspect, there is provided a polymeric stent made from a biodegradable polymer, such as polylactic acid, wherein a pattern is formed using a second harmonic generator laser in which a wavelength of 940 nm to 1,552 nm is converted, and a variation in polydispersity index (PDI) represented by the following Equation 1 is 20% or less:

$$\text{Variation in Polydispersity Index } (\%) = \frac{B-A}{A} \times 100, \quad \text{Equation 1}$$

in Equation 1,

A is a polydispersity index of a polymeric stent before a pattern is formed, and B is a polydispersity index of the polymeric stent after the pattern is formed.

An exemplary embodiment of the present specification is advantageous in that when a pattern is formed on a polymeric stent, the thermal injury of the polymeric stent is minimal.

An exemplary embodiment of the present specification is advantageous in that when a pattern is formed on a polymeric stent, the polymeric stent shows low degradation.

DETAILED DESCRIPTION

Hereinafter, the present specification will be described in detail.

The present specification provides a method for manufacturing a polymeric stent, the method including: manufacturing the polymeric stent by forming a pattern on a polylactic acid tube with a second harmonic generator laser.

The second harmonic generator laser refers to a laser of which the wavelength is divided in half using a second harmonic generator (SHG).

In an exemplary embodiment of the present specification, the pattern may be formed on the polylactic acid tube using a second harmonic generator laser in which a wavelength of 940 nm to 1,552 nm is converted.

Specifically, the pattern may be formed on the polylactic acid tube using a laser in which the wavelength of a laser having a wavelength of 940 nm to 1,552 nm is divided in half through a second harmonic generator (SHG). More specifically, the pattern may be formed on the polylactic acid tube using a laser in which the wavelength of a laser having a wavelength of 1,000 nm to 1,100 nm is divided in half through the second harmonic generator (SHG).

In the present specification, the kind of laser having the wavelength is not particularly limited as long as the wavelength is in a range 940 nm to 1,552 nm. For example, the laser may be any one of neodymium-doped laser, ytterbium-doped laser, erbium-doped laser and hybrid fiber laser.

In the present specification, the wavelength of the second harmonic generator laser may be 470 nm to 776 nm.

In an exemplary embodiment of the present specification, the pattern may be formed on the polylactic acid tube using a second harmonic generator laser in which a wavelength of 940 nm to 1,552 nm is converted.

In the present specification, the wavelength of the second harmonic generator laser may be 500 nm to 550 nm, if necessary.

Recently, the case where a polymeric stent is manufactured by a biodegradable polymer which may be degraded in vivo has increased. In this case, a biodegradable polymer such as polylactic acid is sensitive to an external environment such as heat, moisture and light, and the molecular weight of the biodegradable polymer greatly affects the performance of a polymeric stent, such as mechanical strength and biodegradation rate.

Accordingly, the molecular weight of the biodegradable polymer needs to be adjusted in order to secure the mechanical strength of the polymeric stent and optimize the biodegradation rate. For example, it is important to design a process of manufacturing the polymeric stent such that heat, moisture and the like are adjusted and the molecular weight of the biodegradable polymer is not inhibited.

For example, in a process of forming a pattern on a polymeric tube with laser during the process of manufacturing a polymeric stent, when a biodegradable polymer stent with a laser having a long pulse is processed, there is a disadvantage in that the processed surface becomes molten by heat during the processing (heat affected zone) and the molecular weight of the biodegradable polymer is rapidly decreased.

Meanwhile, when the biodegradable polymeric stent is processed with an ultra-short pulse laser, studies on the change in properties of the biodegradable polymeric stent according to the change in wavelength of the ultra-short pulse laser have been insufficiently conducted to date.

Therefore, in the present specification, the present inventors have studied the change in properties of the biodegradable polymeric stent according to the change in wavelength of the ultra-short pulse laser, particularly, the change in properties of a polylactic acid polymeric stent according to the change in wavelength of the ultra-short wavelength laser.

In the present specification, when a pattern is formed on a polylactic acid tube using the second harmonic generator laser having a wavelength range of 470 nm to 776 nm, there is an advantage in that the thermal injury of the polylactic acid polymer is low at a cut surface of the polylactic acid tube which has been contacted by the second harmonic generator laser.

In the present specification, when a pattern is formed on a polylactic acid tube using the second harmonic generator laser having a wavelength range of 470 nm to 776 nm, there is an advantage in that the degradation of the polylactic acid polymer is low at a cut surface of the polylactic acid tube which has been contacted by the second harmonic generator laser.

In the present specification, when a pattern is formed on a polylactic acid tube using the second harmonic generator laser having a wavelength range of 470 nm to 776 nm, there is an advantage in that the change in molecular weight of the polylactic acid polymer is low at a cut surface of the polylactic acid tube which has been contacted by the second harmonic generator laser.

In the present specification, a variation in polydispersity index (PDI) of the polymeric stent, which is represented by the following Equation 1, may be 20% or less.

$$\text{Variation in Polydispersity Index } (\%) = \frac{B - A}{A} \times 100. \quad \text{[Equation 1]}$$

In Equation 1,

A is a polydispersity index of a polylactic acid tube before a pattern is formed on the polylactic acid tube, and B is a polydispersity index of the polymeric stent after the pattern is formed on the polylactic acid tube.

In the present specification, a variation in average molecular weight of the polymeric stent, which is represented by the following Equation 2, may be 20% or less.

$$\text{Variation in Average Molecular Weight } (\%) = \frac{C - D}{C} \times 100. \quad \text{[Equation 2]}$$

In Equation 2,

C is an average molecular weight of a polylactic acid tube before a pattern is formed on the polylactic acid tube, and D is an average molecular weight of the polymeric stent after the pattern is formed on the polylactic acid tube.

Herein, the variation in average molecular weight may be a variation in number average molecular weight or a variation in mass average molecular weight.

In the present specification, a polydispersity index of the polymeric stent on which the pattern is formed may be 1 to 2.

Herein, a polydispersity index means a value obtained by dividing a mass average molecular weight by a number average molecular weight, indicating that a dispersion of the molecular weight is narrow as the value is closer to 1.

In the present specification, a pulse width of the second harmonic generator laser may be 10 pico-second (ps) or less. Specifically, a pulse width of the second harmonic generator laser may be 1 pico-second (ps) or less. If necessary, a pulse width of the second harmonic generator laser may be 900 femto-second (fs) or less. The lower limit of the pulse width of the second harmonic generator laser is not particularly limited as long as the value is 10 ps or less, but may be, for example, 1 fs or more.

Herein, a pulse refers to a waveform in which the amplitude appears with an impact only within a short time at a constant interval, and a width of the pulse means an interval between a time when the amplitude of the pulse becomes ½ in a rise time and a time when the amplitude of the pulse becomes ½ in a fall time.

In the present specification, a width of the pulse of the laser may be 1 fs to 900 fs before or after being converted into the second harmonic wave.

In the present specification, a repetition rate of the laser may be 2 kHz to 200 kHz before or after being converted into the second harmonic wave.

In the present specification, the power of the laser may be 0.1 W to 10 W before or after being converted into the second harmonic wave.

In the present specification, a spot size of the second harmonic generator laser may be 1 μm to 50 μm.

In the forming of the pattern, the pattern formed on the surface of the polymeric stent is not particularly limited, and a pattern generally used in the art may be adopted.

For example, the pattern may include a V-letter closed figure.

In an exemplary embodiment of the present specification, the method may include manufacturing a polylactic acid tube before the forming of the pattern.

The manufacturing of the polylactic acid tube may include: manufacturing the polylactic acid tube by extruding a molten polylactic acid polymer; and expanding a diameter of the extruded polylactic acid tube.

In the present specification, since the expanding of the diameter of the polylactic acid tube is determining the diameter of the polylactic acid tube in the forming of the pattern, the diameter of the expanded polylactic acid tube is the same as that of the polylactic acid tube prepared for the forming of the pattern.

In the expanding of the diameter of the polylactic acid tube, the outer diameter of the expanded polylactic acid tube may be the same as or smaller than the inner diameter of the blood vessels.

The inner diameter of the blood vessels may vary depending on the blood vessel into which the polymeric stent is inserted. For example, when the blood vessel into which the polymeric stent is inserted is a coronary artery, the diameter of the blood vessel may be 2.5 mm to 4.0 mm.

In the present specification, the outer diameter of the expanded polylactic acid tube may be 0.3× to 1× of the inner diameter of the blood vessel. If necessary, the outer diameter may be 0.4× to 0.7× of the inner diameter of the blood vessel.

In the present specification, it is preferred that the melting point of the polylactic acid polymer exceeds 115° C. When the polylactic acid polymer has a melting point of 115° C. or less, there is a disadvantage in that the mechanical strength is low and the biodegradation rate is fast.

An exemplary embodiment of the present specification may further include applying a composition for preventing restenosis on the surface of the polymeric stent on which the pattern is formed.

The thickness of the composition applied on the polymeric stent on which the pattern is formed may be 2 μm to 30 μm.

The composition for preventing restenosis may be applied on a part or all of the surface of the polymeric stent on which the pattern is formed.

The composition for preventing restenosis may be applied at least on an outer side surface or an inner side surface of the surface of the polymeric stent on which the pattern is formed.

The composition for preventing restenosis may be applied on the entire surface of the polymeric stent on which the pattern is formed.

The composition for preventing restenosis is not particularly limited as long as the composition includes a compound capable of preventing restenosis.

For example, the composition for preventing restenosis may include a Rapamycin-based compound. For example, the Rapamycin-based compound may be Sirolimus, Everolimus, Biolimus, Zotarolimus and the like.

In an exemplary embodiment of the present specification, the composition for preventing restenosis may include at least one Rapamycin-based compound selected from Sirolimus, Everolimus, Biolimus and Zotarolimus.

The composition for preventing restenosis may further include a polymer and a solvent.

The polymer is not particularly limited as long as the polymer may impart adhesion property to the surface of the polymeric stent.

The polymer may be the same as or similar to a polymer constituting the polymeric stent. For example, when a material for the polymeric stent includes a polylactic acid-based polymer, a polymer included in the composition for preventing restenosis may include a polylactic acid-based polymer.

The solvent is not particularly limited, and may be selected among those used in the art. For example, the solvent may include one or two or more from acetone, methanol and ethanol.

The concentration of the solute except for the solvent in the composition for preventing restenosis may be 0.1% by weight to 5% by weight.

An exemplary embodiment of the present specification may further include compressing the polymeric stent on which the composition for preventing restenosis is applied in a radius direction.

In the compressing step, compression is performed such that the form of the circular cross-sectional surface of the polymeric stent is maintained. Specifically, the compressing is performed by applying force to all the radial directions of the polymeric stent. Herein, the radius direction refers to a direction from the circumference of the circle to the center of the circle on the cross-sectional surface perpendicular to the longitudinal direction of the polymeric stent.

The temperature in the compressing step may be higher than the body temperature and lower than the glass transition temperature of the polymeric stent. In this case, the body temperature is a temperature of blood in the blood vessel into which the polymeric stent is inserted, but specifically, the body temperature may be more than 36° C. and less than 39° C., and the glass transition temperature of the polymeric stent may be about 60° C.

In the compressing step, the polymeric stent may be compressed in all the radial directions using a crimping head heated to a temperature which is higher than the body temperature and lower than the glass transition temperature of the polymeric stent.

The outer diameter of the polymeric stent compressed in the compressing step may be 1 mm to 1.6 mm.

Before the polymeric stent is compressed in the compressing step, a balloon may be inserted into the inside of the polymeric stent, and then the polymeric stent may be compressed.

When a balloon is inserted into the inside of the polymeric stent before the polymeric stent is compressed, a delivery device is used to position the polymeric stent in the compressed state to a treatment site, and then the polymeric stent may be mechanically expanded with the aid of an inflatable balloon, within the body vessel. The delivery device is then detached from the polymeric stent, and the polymeric stent remains within the body vessel at the treatment site as an implant.

The method for manufacturing a polymeric stent may further include forming a groove or a hole on at least one of the struts of the polymeric stent on which the pattern is formed, and affixing a radiomarker to the groove or the hole.

Figure 8:
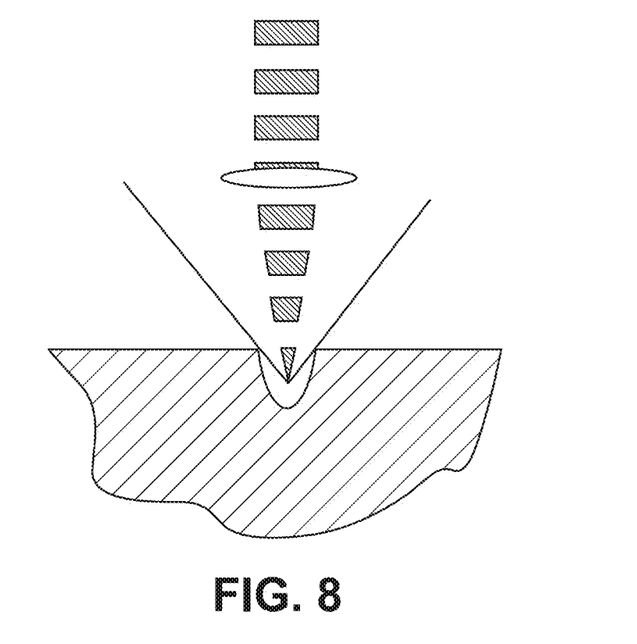
FIG. 8 illustrates an exemplary embodiment in which a groove is formed on the surface of a polymeric stent using ultra-short pulse laser.

In the forming of the groove or the hole, it is possible to use an ultra-short pulse laser to form a groove which does not pass through the strut as illustrated in FIG. 8 or form a hole which passes through the strut.

Figure 9:
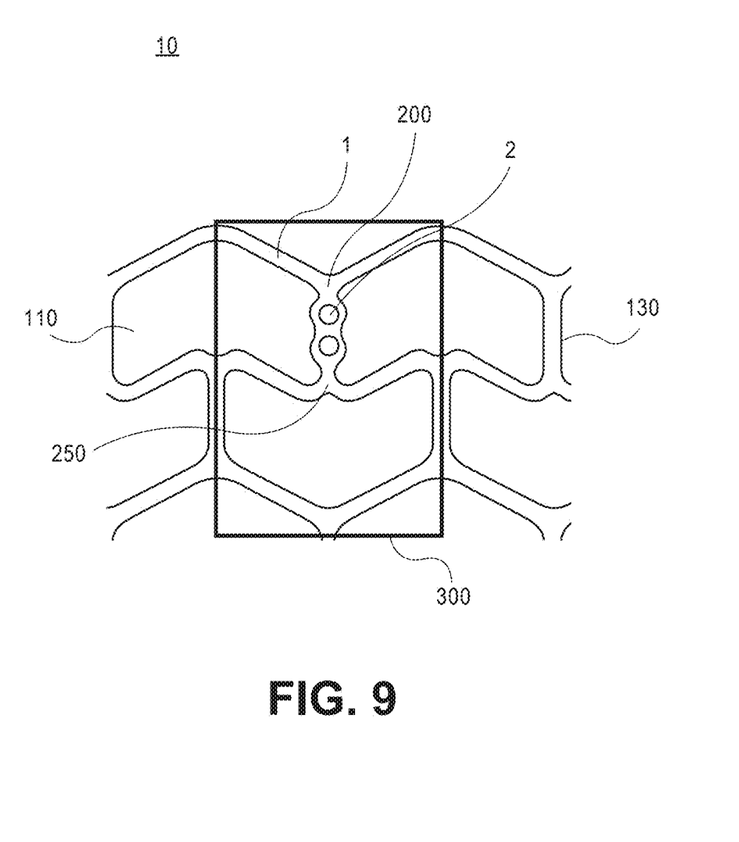
FIG. 9 illustrates an exemplary embodiment in which a radiomarker is adhered to a groove formed on a strut of a polymeric stent using a melt gun.

In the affixing of the radiomarker, it is possible to use polylactic acid molten at 115° C. to 240° C. to affix a radiomarker to the groove as illustrated in FIG. 9. When polylactic acid is molten at a temperature more than 240° C. to adhere the radiomarker, the molecular weight of the polylactic acid molten is rapidly decreased, and polylactic acid molten at a temperature less than 115° C. is not suitable because of low mechanical strength and high biodegradation rate.

In this case, it is possible to use a melt gun by which polylactic acid molten at 115° C. to 240° C. is applied.

When polylactic acid is molten at a temperature more than 240° C. to adhere the radiomarker, the molecular weight of the polylactic acid molten is rapidly decreased, and polylactic acid molten at a temperature less than 115° C. is not suitable because of low mechanical strength and high biodegradation rate.

It is preferred that the melting point of polylactic acid used to affix the radiomarker in the affixing of the radiomarker exceeds 115° C. When the polylactic acid used herein has a melting point of 115° C. or less, there is a disadvantage in that the mechanical strength is low and the biodegradation rate is fast.

When the stent is generally inserted into and present within body vessels, radiation such as X-ray is irradiated to the human body in order to know the position and the like of the polymeric stent. However, since the polymeric stent is generally radiolucent and transmits radiation, the position cannot be detected by radiation.

Accordingly, in order to detect the position of the polymeric stent, a radiomarker including a radiopaque material which reflects radiation may be attached or fused to one or more struts in the polymeric stent.

As illustrated in FIG. 9, a radiomarker 2 including a radiopaque material may be attached or fused to at least one strut 1 of a polymeric stent 10.

The present specification provides a polymeric stent manufactured by the method for manufacturing a polymeric stent.

In the present specification, the polydispersity index of the polymeric stent may be 1 to 2.

Further, the present specification provides a polymeric stent in which a pattern is formed using a second harmonic generator laser in which a wavelength of 940 nm to 1,552 nm is converted, and a variation in polydispersity index (PDI) represented by the following Equation 1 is 20% or less.

$$\text{Variation in Polydispersity Index } (\%) = \frac{B-A}{A} \times 100. \quad \text{[Equation 1]}$$

In Equation 1,

A is a polydispersity index of a polymeric stent before a pattern is formed, and B is a polydispersity index of the polymeric stent after the pattern is formed.

In the present specification, the polydispersity index of the polymeric stent may be 1 to 2.

In addition, the present specification provides a polymeric stent in which a pattern is formed using a second harmonic generator laser in which a wavelength of 940 nm to 1,552 nm is converted, a variation in polydispersity index (PDI) represented by the following Equation 1 is 20% or less, and a variation in average molecular weight represented by the following Equation 2 is 20% or less.

$$\text{Variation in Polydispersity Index } (\%) = \frac{B-A}{A} \times 100. \quad \text{[Equation 1]}$$

In Equation 1,

A is a polydispersity index of a polymeric stent before a pattern is formed, and B is a polydispersity index of the polymeric stent after the pattern is formed.

$$\text{Variation in Average Molecular Weight } (\%) = \frac{D-C}{C} \times 100. \quad \text{[Equation 2]}$$

In Equation 2,

C is an average molecular weight of a polymeric stent before a pattern is formed, and D is an average molecular weight of the polymeric stent after the pattern is formed.

Furthermore, the present specification provides a polymeric stent in which a pattern is formed using a second harmonic generator laser in which a wavelength of 940 nm to 1,552 nm is converted, and a variation in average molecular weight represented by the following Equation 2 is 20% or less.

$$\text{Variation in Average Molecular Weight } (\%) = \frac{D-C}{C} \times 100. \quad \text{[Equation 2]}$$

In Equation 2,

C is an average molecular weight of a polymeric stent before a pattern is formed, and D is an average molecular weight of the polymeric stent after the pattern is formed.

The description on the polymeric stent is the same as what is described above in the method for manufacturing a polymeric stent.

Hereinafter, the present specification will be described in detail with respect to the Examples. The following Examples are for describing the present specification, and the scope of the present specification includes the scope described in the following claims and the substitutions and modifications thereof, and is not limited to the scope of Examples.

EXAMPLES

Example 1

A second harmonic generator was used to convert a laser having a wavelength of 1,030 nm into a second harmonic generator laser having a wavelength of 515 nm and a pattern was formed on a polylactic acid tube with a second harmonic generator laser having a wavelength of 515 nm.

Physical properties of the laser having a wavelength of 1,030 nm are as follows.

Spot Size=21.5 μm
Average Power=0.18 Watt
Repetition Rate=30 KHz
Speed=2.1 mm/sec Comparative Example 1

A process was performed in the same manner as in Example 1, except that a third harmonic generator was used to convert a laser having a wavelength of 1,030 nm into a third harmonic generator laser having a wavelength of 343 nm and a pattern was formed on a polylactic acid tube with a third harmonic generator laser having a wavelength of 343 nm.

Herein, the third harmonic generator refers to a device which divides the wavelength of the laser into ⅓.

Comparative Example 2

A process was performed in the same manner as in Example 1, except that a pattern was formed on a polylactic acid tube with a laser having a wavelength of 1,030 nm without using the second harmonic generator.

Experimental Example 1

SEM Observation

While forming the pattern with the laser in Example 1 and Comparative Examples 1 and 2, a surface exposed by cutting the polylactic acid tube was each captured by a scanning electron microscope (SEM) and observed.

Figure 1:
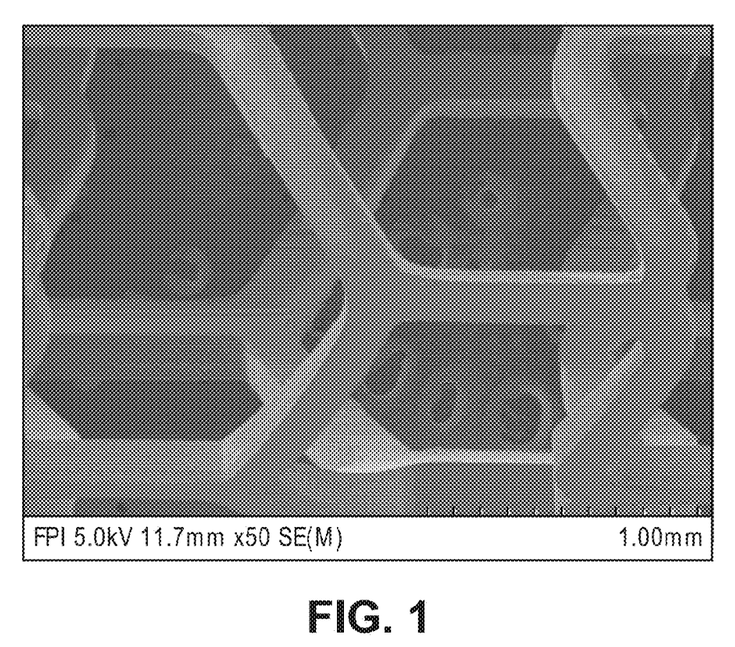
FIG. 1 is a scanning electron microscope (SEM) photograph of a polymeric stent in which a pattern of Example 1 is formed.
Figure 2:
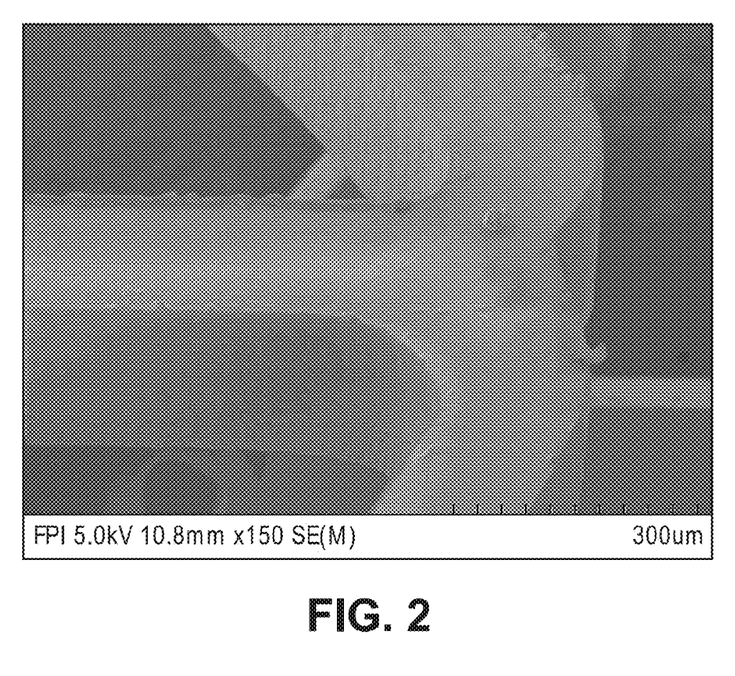
FIGS. 2 and 3 are SEM photographs taken of a cut surface of the polymeric stent in which the pattern of Example 1 is formed.
Figure 3:
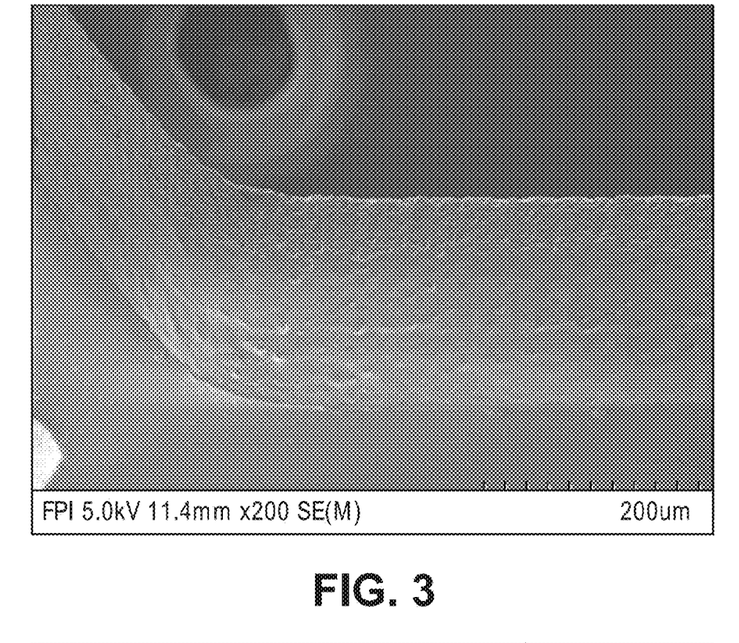

A photograph taken of the cut surface of Example 1 is illustrated in FIGS. 1 to 3.

FIG. 1 is a SEM photograph of Example 1, and one side surface of a polymeric stent on which a pattern is formed was observed.

FIG. 2 is a SEM photograph of Example 1, a connecting part of struts in a polymeric stent on which a pattern was formed was observed, and it can be seen that the cut surface of the strut and the surrounding portions were cleanly cut.

FIG. 3 is a SEM photograph of Example 1, a cut surface of a polymeric stent on which a pattern was formed was observed, and it can be seen that the polymeric stent was cut without an injury by heat.

Figure 4:
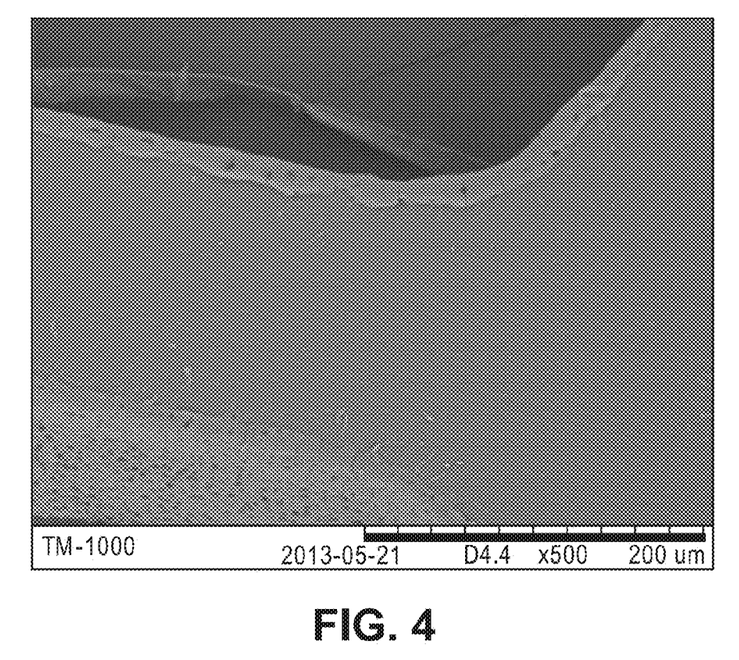
FIGS. 4 and 5 are SEM photographs taken of a cut surface of a polymeric stent in which a pattern of Comparative Example 1 is formed.
Figure 5:
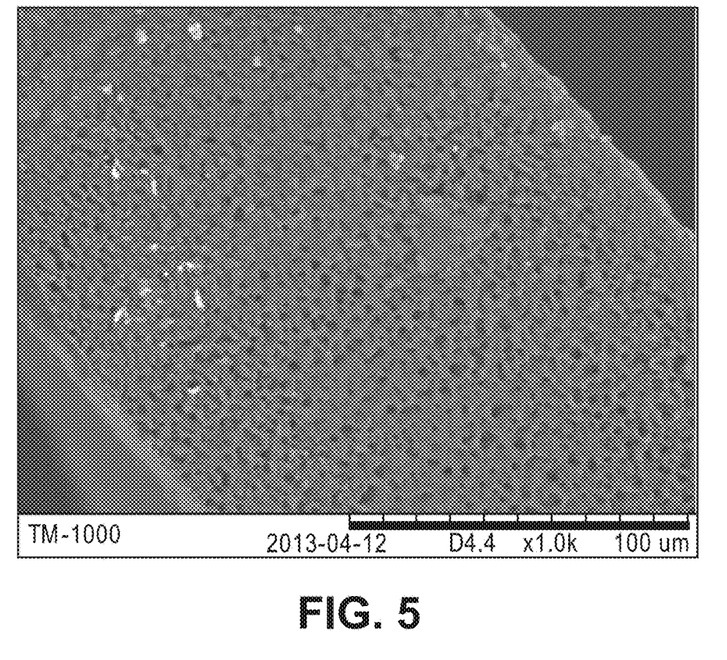

A photograph taken of the cut surface of Comparative Example 1 is illustrated in FIGS. 4 to 5.

FIG. 4 is a SEM photograph of Comparative Example 1, a connecting part of struts in a polymeric stent on which a pattern was formed was observed, and it can be seen that the surrounding portions of the cut surface of the strut were polymer-modified.

FIG. 5 is a SEM photograph of Comparative Example 1, a cut surface of a polymeric stent on which a pattern was formed was observed, and it can be seen that the cut surface was relatively cleanly cut.

Figure 6:
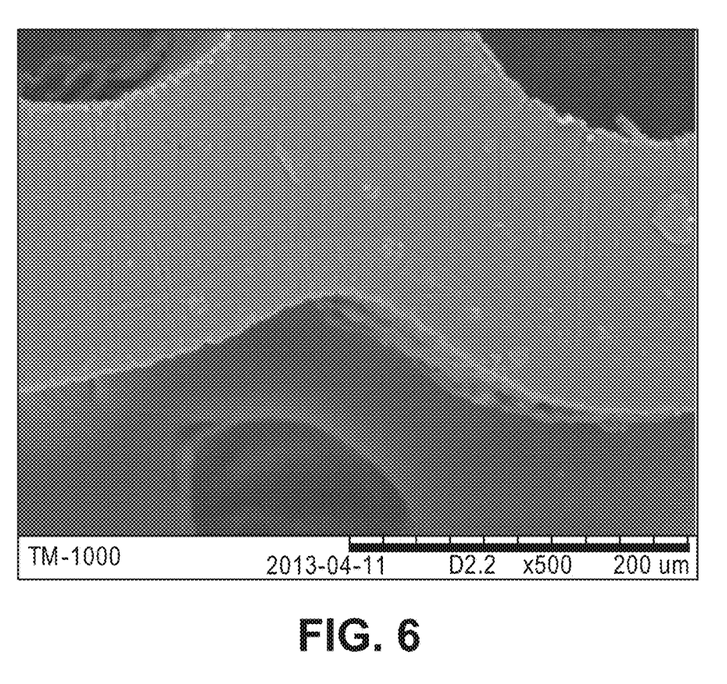
FIG. 6 is a SEM photograph taken of a cut surface of a polymeric stent in which a pattern of Comparative Example 2 is formed.
Figure 7:
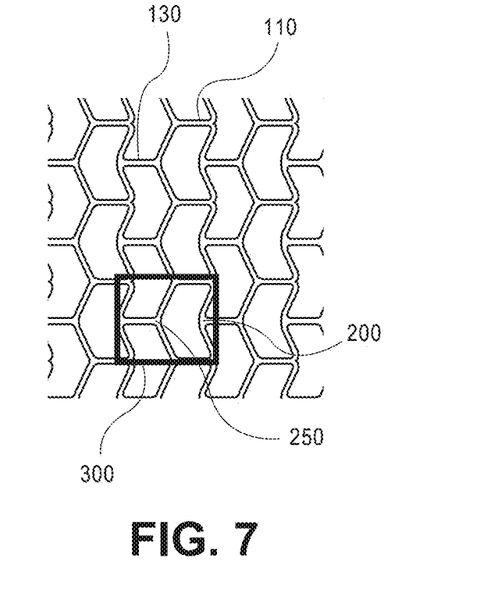
FIG. 7 illustrates an exemplary embodiment of a pattern of a polymeric stent according to the present specification.

A photograph taken of the cut surface of Comparative Example 2 is illustrated in FIG. 6. FIG. 6 is a SEM photograph of Comparative Example 2, and it can be seen that the cut surface of the polymeric stent on which the pattern was formed was not clean and heat modification occurred at the cut surface.

Experimental Example 2

Gel permeation chromatography (GPC) was used to measure the number average molecular weight (Mn) and the polydispersity index (PDI, Mw/Mn) of a polylactic acid (PLA) tube before the laser processing and of a polylactic acid stent after the laser processing in Example 1, Comparative Example 1 and Comparative Example 2. The variation in polydispersity index (PDI) represented by the following Equation 1, and the variation in average molecular weight represented by the following Equation 2 are calculated.

$$\text{Variation in Polydispersity Index } (\%) = \frac{B-A}{A} \times 100. \quad \text{Equation 1}$$

In Equation 1,

A is a polydispersity index of a polylactic acid (PLA) tube before a pattern is formed on the polylactic acid tube, and B is a polydispersity index of the polylactic acid (PLA) polymeric stent after the pattern is formed on the polylactic acid tube.

$$\text{Variation in Average Molecular Weight } (\%) = \frac{C-D}{C} \times 100. \quad \text{Equation 2}$$

In Equation 2,

C is an average molecular weight of a polylactic acid tube before a pattern is formed, and D is an average molecular weight of the polymeric stent after the pattern is formed.

In this case, an HFIP gel column (Agilent) was used as a column in the measurement of GPC, and a solution in which 10 mM of sodium trifluoroacetate was dissolved in hexafluoroisopropanol (HFIP) was used as an eluent at a transport speed of 0.2 ml/min.

The results measured by GPC are shown in the following Table 1.

TABLE 1

|  | Example 1 | | Comparative Example 1 | | Comparative Example 2 | |
| --- | --- | --- | --- | --- | --- | --- |
|  | Mn (KDa) | Mw/Mn | Mn (KDa) | Mw/Mn | Mn (KDa) | Mw/Mn |
| PLA tube expanded before laser processing | 222 | 1.5 | 167 | 1.9 | 167 | 1.9 |
| PLA stent processed with laser | 195 | 1.6 | 28 | 4.6 | 129 | 2.3 |
| Variation in PDI | 6.67% | | 142.11% | | 21.05% | |
| Variation in Mn | 12.16% | | 83.23% | | 22.75% | |

As shown in Table 1, it can be seen that in Example 1, there was almost no change in variation in the molecular weight after a pattern was formed.

However, it can be seen that in Comparative Example 1, the molecular weight was rapidly decreased after the pattern was formed, and the polydispersity index was significantly increased. Since the C═O bond of polylactic acid has absorption bands at the wavelength ranges of 280 nm and 190 nm and the C—C bond and the C—H bond of polylactic acid absorb the wavelength shorter than 180 nm, when processing was performed with a femto second laser at the wavelength ranges shorter than the ultraviolet rays or the ultraviolet rays, the wavelength is absorbed and polylactic acid became photodegraded. Accordingly, the femto second laser having the wavelength ranges shorter than the ultraviolet rays or the ultraviolet rays is not appropriate for processing the polylactic acid stent.

Further, in Comparative Example 2, it can be seen that a variation in polydispersity index was significant, and as a result, it can be seen that the distribution of molecular weights was broadened.

Experimental Example 3

An ultra-short pulse laser (laser having a pulse width of pico seconds or less) was used to form a groove in a strut of a polylactic acid stent as illustrated in FIG. 8. In order to affix a radiomarker to the groove, a melt gun by which polylactic acid was molten at a temperature 115° C. to 240° C. was used to adhere the radiomarker to a strut of a polylactic acid stent in which the groove is formed, as illustrated in FIG. 9. When polylactic acid is molten at a temperature more than 240° C. to adhere the radiomarker, the molecular weight of polylactic acid is rapidly decreased, and polylactic acid molten at less than 115° C. is not suitable because of low mechanical strength and high biodegradation rate.

In FIG. 9, the numbers represent the following structures: (1) strut; (2) radiomarker; (10) polymeric stent; (110) unit cell; (130) linker portion; (200) first hinge portion; (250) second hinge portion; and (300) repeating unit.

What is claimed is:

1. A polymeric stent, wherein the polymeric stent comprises a polylactic acid tube and wherein a pattern is cut on the polylactic acid tube using a second harmonic generator laser in which a first wavelength of 940 nm to 1,552 nm is converted to a second wavelength of 470 nm to 776 nm, wherein a pulse width of the second harmonic generator laser is 1 fs to 900 fs and wherein a repetition rate of the second harmonic generator laser is 2 kHz to 200 kHz, and wherein the polymeric stent comprises a variation in polydispersity index (PDI), represented by the following Equation 1, of 20% or less:

$$\text{Variation in Polydispersity Index} (\%) = \frac{B-A}{A} \times 100, \quad \text{Equation 1}$$

wherein in Equation 1,

A is a polydispersity index of the polymeric stent before the pattern is cut on the polylactic acid tube, and B is a polydispersity index of the polymeric stent after the pattern is cut on the polylactic acid tube.

2. The polymeric stent of claim 1, wherein the polydispersity index of the polymeric stent after the pattern is cut on the polylactic acid tube, is 1 to 2.

3. The polymeric stent of claim 1, wherein the variation in average molecular weight of the polymeric stent represented by the following Equation 2 is 20% or less:

$$\text{Variation in Average Molecular Weight} (\%) = \frac{C-D}{C} \times 100, \quad \text{Equation 2}$$

wherein in Equation 2,

C is an average molecular weight of the polymeric stent before the pattern is cut on the polylactic acid tube, and D is an average molecular weight of the polymeric stent after the pattern is cut on the polylactic acid tube.

4. The polymeric stent of claim 1, wherein the pattern is cut on the polylactic acid tube using a second harmonic generator laser in which a wavelength of 1000 nm to 1,100 nm is converted to a second wavelength of 500 nm to 550 nm.

* * * * *